United States Patent
Schertiger et al.

(10) Patent No.: US 11,931,524 B2
(45) Date of Patent: Mar. 19, 2024

(54) URINARY CATHETERISATION AID

(71) Applicant: Coloplast A/S, Humlebaek (DK)

(72) Inventors: Lars Olav Schertiger, Fredensborg (DK); Alistair David Morton, Kastrup (DK); Berker Diker, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 80 days.

(21) Appl. No.: 17/433,604

(22) PCT Filed: Feb. 25, 2020

(86) PCT No.: PCT/DK2020/050050
§ 371 (c)(1),
(2) Date: Aug. 25, 2021

(87) PCT Pub. No.: WO2020/173531
PCT Pub. Date: Sep. 3, 2020

(65) Prior Publication Data
US 2022/0134054 A1     May 5, 2022

(30) Foreign Application Priority Data
Feb. 25, 2019 (DK) .......................... PA 2019 70116

(51) Int. Cl.
*A61M 25/01* (2006.01)
*A61M 25/00* (2006.01)

(52) U.S. Cl.
CPC ....... *A61M 25/0111* (2013.01); *A61M 25/002* (2013.01); *A61M 25/007* (2013.01); *A61M 25/0113* (2013.01); *A61M 2025/0175* (2013.01); *A61M 2210/1092* (2013.01)

(58) Field of Classification Search
CPC .................. A61M 25/0111; A61M 2210/1092
See application file for complete search history.

(56) References Cited

U.S. PATENT DOCUMENTS

| | | | |
|---|---|---|---|
| 5,045,078 A | 9/1991 | Asta | |
| 5,084,036 A * | 1/1992 | Rosenbaum | A61M 25/01 604/329 |
| 5,653,700 A | 8/1997 | Byrne et al. | |
| 5,779,670 A | 7/1998 | Bidwell et al. | |
| 8,998,883 B1 | 4/2015 | Feloney | |
| 9,108,020 B1 * | 8/2015 | Feloney | A61M 25/0043 |
| 2003/0018322 A1 * | 1/2003 | Tanghoj | A61M 25/0111 604/544 |
| 2006/0025753 A1 | 2/2006 | Kubalak et al. | |
| 2009/0071851 A1 | 3/2009 | Maki et al. | |
| 2010/0256580 A1 | 10/2010 | Faber | |
| 2011/0040290 A1 | 2/2011 | Zadini et al. | |

(Continued)

FOREIGN PATENT DOCUMENTS

BR    MU8302415 U    5/2005
CN    106345039 A    1/2017
(Continued)

*Primary Examiner* — Ariana Zimbouski
*Assistant Examiner* — Matthew Wrubleski
(74) *Attorney, Agent, or Firm* — Coloplast Corp., Coloplast A/S; Nick Baumann

(57) ABSTRACT

An intermittent urinary catheterisation aid 2 and an assembly is provided. The aid allows a user to manipulate an intermittent urinary catheter 3 in one direction and insert it into the urethra in another direction.

11 Claims, 4 Drawing Sheets

(56) References Cited

U.S. PATENT DOCUMENTS

| | | |
|---|---|---|
| 2013/0006226 A1 | 1/2013 | Hong et al. |
| 2014/0257250 A1 | 9/2014 | Palmer |
| 2015/0133898 A1 | 5/2015 | Murray et al. |
| 2015/0320970 A1 | 11/2015 | Foley et al. |
| 2016/0022959 A1 | 1/2016 | Schertiger et al. |
| 2016/0038717 A1 | 2/2016 | Murray et al. |
| 2016/0067445 A1 | 3/2016 | Murray et al. |
| 2016/0136391 A1 | 5/2016 | Foley et al. |
| 2017/0291011 A1 | 10/2017 | McMenamin et al. |

FOREIGN PATENT DOCUMENTS

| | | |
|---|---|---|
| DE | 10000975 C1 | 9/2001 |
| DE | 202005009947 U1 | 9/2005 |
| WO | 04054653 A1 | 7/2004 |

\* cited by examiner

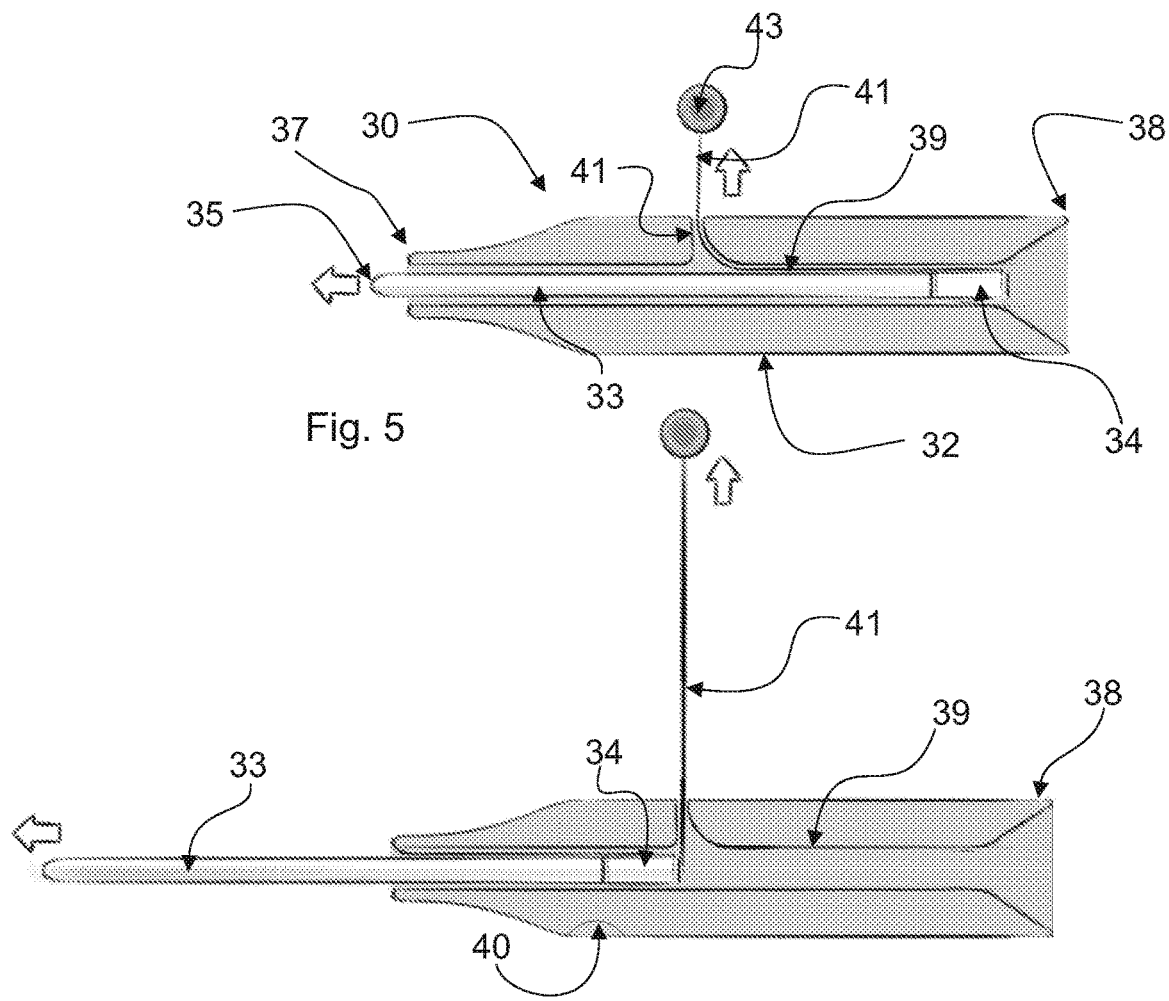
Fig. 5
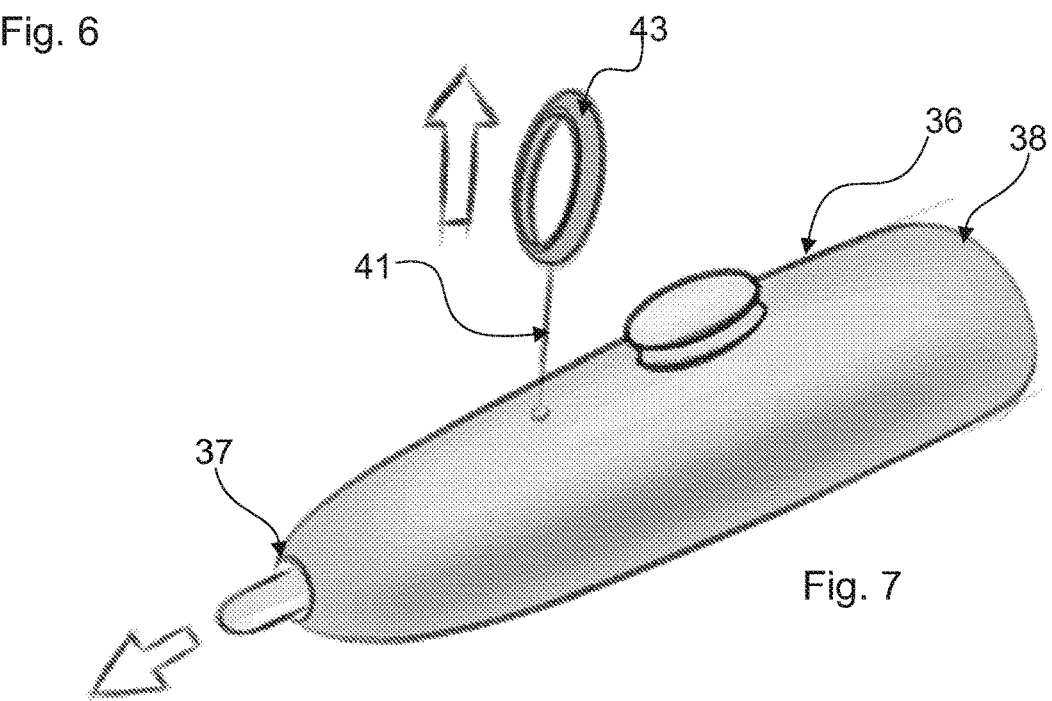
Fig. 6
Fig. 7

URINARY CATHETERISATION AID

The invention relates to a urinary catheter assembly and a urinary catheterisation aid. The assembly and aid are particularly useful in relation with intermittent self-catheterisation of females, where the limited room inside the toilet bowl is an issue.

BRIEF DESCRIPTION OF THE DRAWING

The accompanying drawings are included to provide a further understanding of embodiments and are incorporated into and are a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

In FIG. 1, a side view of an embodiment is shown. In FIG. 2, a perspective schematic view of an embodiment is shown. FIGS. 3 and 4 show schematic cross-sectional views of the embodiment.

FIGS. 5-7 illustrate an intermittent urinary catheter assembly. FIGS. 5-6 illustrate schematic cross-sectional views and FIG. 7 illustrates a schematic perspective view.

FIG. 8 illustrates a side view in a closed, storage configuration and FIG. 9 illustrates a side view in an open configuration, when the catheter is ready to be inserted.

DETAILED DESCRIPTION

Figure 1:
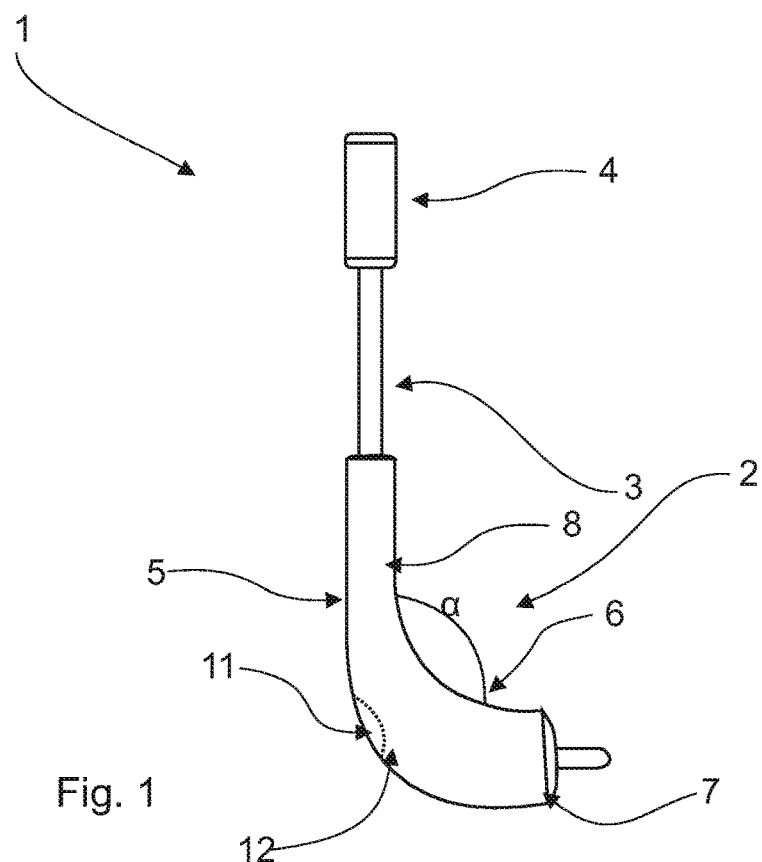
FIGS. 1-4 illustrates an embodiment of an intermittent urinary catheter assembly.

Embodiments relate to a urinary catheterization aid comprising a handle having a distal end and a proximal end and an insertion guide having a distal end and a proximal end, the handle and insertion guide having a guiding channel extending therethrough from the distal end of the handle to the proximal end of the insertion guide, the guiding channel being adapted for having an intermittent urinary catheter entered through the guiding channel, the handle and the insertion guide being disposed at a first angle of between 45 and 135 degrees with respect to each other so that an intermittent urinary catheter can enter the handle in a first direction and exit the insertion guide in a second direction at the first angle to the first direction.

Embodiments relate to a method of inserting an intermittent urinary catheter by using the urinary catheterization aid such that the user manipulates the catheter in the first direction and is able to insert the catheter into the urethra in the second direction.

A urinary catheterization aid as defined above provides a device making insertion of a urinary catheter easier, particularly for the female user. Females may experience problems in finding the urethral opening because it is difficult, if not impossible, to see it without a mirror. Furthermore, the limited room inside a toilet bowl may make it difficult for the user to handle and insert the catheter in a sterile manner. For example, if the catheter is around 10 cm long in total, it may be very difficult to find room for the hand and the catheter inside the toilet bowl as the catheter is to be inserted. The catheterization aid having a handle and insertion guide being disposed at a first angle with respect to each other provides for the different directions of movement, so that the user moves the catheter in the first direction and then the catheter moves in the second direction. This means that when the user sits on the toilet, (s)he grabs the handle and may move the catheter in a generally downwards direction corresponding to the first direction. Due to the bend between the handle and insertion guide, the catheter will move in a second direction into the urethra. The user of the catheter will therefore not have to put both hands deep into the toilet bowl, but only needs to control the insertion of the catheter into the urethra with one hand, while the other hand can stay above the toilet bowl and control the movement of the catheter. Thus, the limited room inside the toilet bowl will be less of a problem with such an assembly.

In the following, whenever referring to a proximal end of an element of the invention, the referral is to the end adapted for insertion or closest to the insertion end. Whenever referring to the distal end of an element, the referral is to the end opposite the insertion end. In other words, the proximal end is the end closest to the user, when the catheter is to be inserted, and the distal end is the opposite end, i.e. the end furthest away from the user when the catheter is to be inserted. The same definitions apply to the urinary catheterization aid; the proximal end is the end closest to the user in use, and the distal end is the opposite end. The handle and insertion guide of the urinary catheterization aid are provided with a bend between them. The bend means that the handle is positioned at an angle to the insertion guide. The guiding channel has a first portion longitudinally through the handle, a second portion around the bend and a third portion longitudinally through the insertion guide. This means that a longitudinal axis of the handle defines a first direction of movement and a longitudinal axis of the insertion guide defines a second direction of movement; the second direction of movement will be aligned with the insertion direction of the catheter when a catheter is inserted through the urinary catheterization aid. The first direction is at a first angle to the second direction, the first angle preferably being between 45 and 135 degrees. In the context of this disclosure, the handle is the part which the user holds during use, whereas the insertion guide assists in providing an aligned insertion direction of a catheter.

The catheter described in this application is to be used as an intermittent urinary catheter.

The intermittent urinary catheter comprises a main tubular part extending from the distal end to the proximal end. The tip is positioned in the proximal end of the catheter and is provided as a rounded closed end of the tube constituting the main part of the catheter. The catheter may comprise a handle in the distal end. The handle may be in the form of a connector and may in an embodiment comprise a flared end of the catheter so that the diameter of the connector increases with respect to the tubular part.

Usually catheters used as intermittent urinary catheters are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

Catheters of this invention may prior to use be provided with a hydrophilic coating so as to impart a low-friction insertion.

In an embodiment, the intermittent urinary catheter is a telescopic catheter.

The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use because the surface coating tends to stick inside the mucosa of the urethra if left inside the body for a period exceeding 5-20 minutes due to the hydrophilic coating transforming from being highly lubricious when fully wetted (95% weight water) to being adhesive when the hydration level of the coating is reduced (<75% weight water).

The handle and insertion guide are preferably made integrally with each other such that the urinary catheterization aid consists of a handle and an insertion guide connected through a bend or angled transition portion. The urinary catheterization aid may be made of a thermoplastic material, such as polyethylene (PE), polypropylene (PP) or a thermoplastic elastomeric material (TPE) or combinations of these materials.

The intermittent urinary catheter may be made of a polyurethane material (PU) or polyvinyl chloride (PVC) or poly-olefins such as a polyethylene (PE). Other materials may be silicone materials, latex material, styrenic block copolymers, TPS (TPE-s) (thermoplastic elastomeric materials), thermoplastic vulcanizates, TPV, Thermoplastic copolyester, TPC (TPE-E), thermoplastic polyamides, TPA, (TPE-A).

Embodiments relate to the urinary catheterization aid further comprising an outlet channel extending from the guiding channel to a drainage opening at an outer surface of the urinary catheterization aid so as to allow urine to be drained through the outlet channel.

Providing an outlet channel from the guiding channel to a drainage opening has the advantage of allowing an easy and non-contaminating draining of urine from the guiding channel.

Embodiments relate to the outlet channel extending at a second angle from the guiding channel, the second angle between the outlet channel and the guiding channel being between 90 and 180 degrees.

Positioning the outlet channel at a second angle with respect to the guiding channel has the advantage that the outlet of the assembly allows urine to be securely drained into the toilet. When a female handles a regular female catheter in a straight configuration, a situation may occur where the urine starts to flow before the distal end of the catheter is within the toilet bowl. In such a situation, urine may flow onto the toilet seat or the surroundings of the toilet which, of course, is undesired. By providing an outlet—and in particular with a second angle from the guiding channel, this problem is alleviated.

Embodiments relate to the first angle being between 75 and 105 degrees, such as 80 to 100 degrees such as about 90 degrees. A first angle relatively close to 90 degrees provides for an easy handling of the catheter inside a toilet bowl, because the handle extends close to perpendicular to the second direction, which corresponds to the insertion direction.

Embodiments relate to the second angle being between 105 and 165, such as between 120 and 150 degrees such as about 135 degrees.

Embodiments relate to a urinary catheterization aid, wherein the assembly further comprises a sleeve attached to the handle.

A sleeve attached to the handle provides for an extra security for avoiding touching the outer surface of the catheter during use. The sleeve may be made of a thin PE-foil. The sleeve may be attached to the handle by welding or gluing, which both are well-known processes.

Embodiments relate to a urinary catheterization aid, wherein the assembly further comprises a connector at a distal end of the assembly, the sleeve being attached to the connector.

Such an embodiment has the effect that the sleeve covers (almost) the entire length of the catheter and therefore, there is very little risk of the user touching the outer surface of the catheter by accident. Thus, the insertion of the catheter is hygienic.

Embodiments relate to an intermittent urinary catheter assembly, wherein the connector and handle comprises cooperating means for attaching them to each other so that the handle, sleeve and connector together provides an enclosure for the catheter.

An enclosure for the catheter provided by the sleeve, handle and connector, ensures the sterility of the assembly prior to use. As long as the connector is attached to the handle, any outside material is prevented from coming into contact with the catheter surface. This means that such an assembly has a good sterility barrier.

The cooperating means may be in the form of a bayonet coupling, threads, snap-fit couplings or other well-known interlocking means.

Embodiments relate to an intermittent urinary catheter assembly comprising an intermittent urinary catheter and a urinary catheterization aid as mentioned above, wherein the urinary catheter comprises at least one draining hole at a middle part of the catheter so that urine entering the catheter at a proximal end is able to be drained through the catheter through the draining hole(s) and leave the urinary catheterization aid at the outlet.

Embodiments relate to an intermittent urinary catheter assembly, wherein the intermittent urinary catheter is a female catheter.

In particular for females, the limited room inside the toilet bowl is a significant problem, because of the position of the urethral opening facing downwards into the toilet bowl. Therefore, the intermittent urinary catheter assembly is particularly useful for female use.

In an embodiment, the handle has a length of 7 cm from the distal end to the bend of the handle. It may be shorter such as 5 cm or longer such as 10 cm. It should be so long that it is safely retained inside a human hand, while not being overly long.

In an embodiment, the insertion guide may be between 1 and 3 cm from the distal end to the proximal end. It may be shorter so that the first part just provides a very short angled protrusion. The only requirement for the length of the insertion guide is that it must be able to bend the catheter so that the catheter can be inserted in angled direction as compared to the direction of movement impacted upon the catheter by the user.

In an embodiment, the handle and insertion guide may define an almost continuous curve from the distal end of the handle to the proximal end of the insertion guide. In those embodiments, the overall length of the handle and insertion guide may be 5 cm or less, such as 3-4 cm.

The intermittent urinary catheter may be a telescopic catheter. The telescopic catheter may be in the form of two tubular elements, one having a smaller diameter than the other. For example, the smaller tubular element may correspond to a CH10 catheter and the larger tubular element may correspond to a CH14 catheter. This allows the smaller catheter to be entered into the larger catheter for a compact storing. The two tubular elements may be coupled together such as to allow extension of the catheter into a longer configuration and allow insertion of the proximal tubular element without collapsing of the catheter. An example of a suitable coupling can be found in WO2008138351.

Described is a catheterisation aid, wherein the means for transferring a movement comprises a string attached to the distal end of the catheter, where the string is threaded through a hole in a side of the assembly proximally of the distal end, so that pulling the string in the second direction transfers to movement of the catheter in the first direction.

The string element may be provided with a pull-ring allowing for putting a finger through the pull-ring. Users having poor hand dexterity may find it difficult to pinch and grab a string, thus a pull-ring is easier to use for such users.

DETAILED DESCRIPTION OF THE DRAWING

Embodiments, and features of the various exemplary embodiments described in this application, may be combined with each other ("mixed and matched"), unless specifically noted otherwise.

Figure 2:
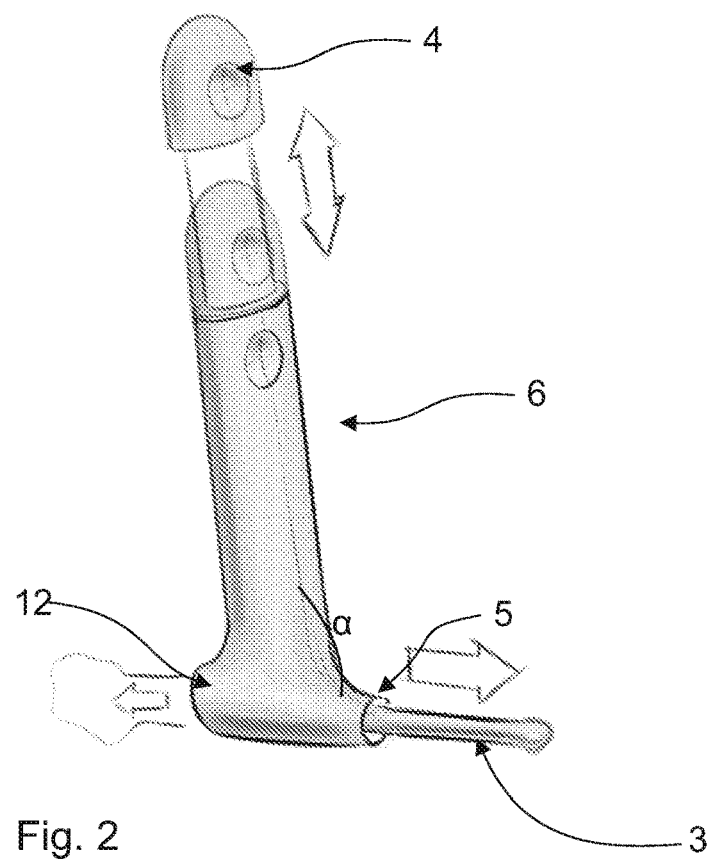
Figure 3:
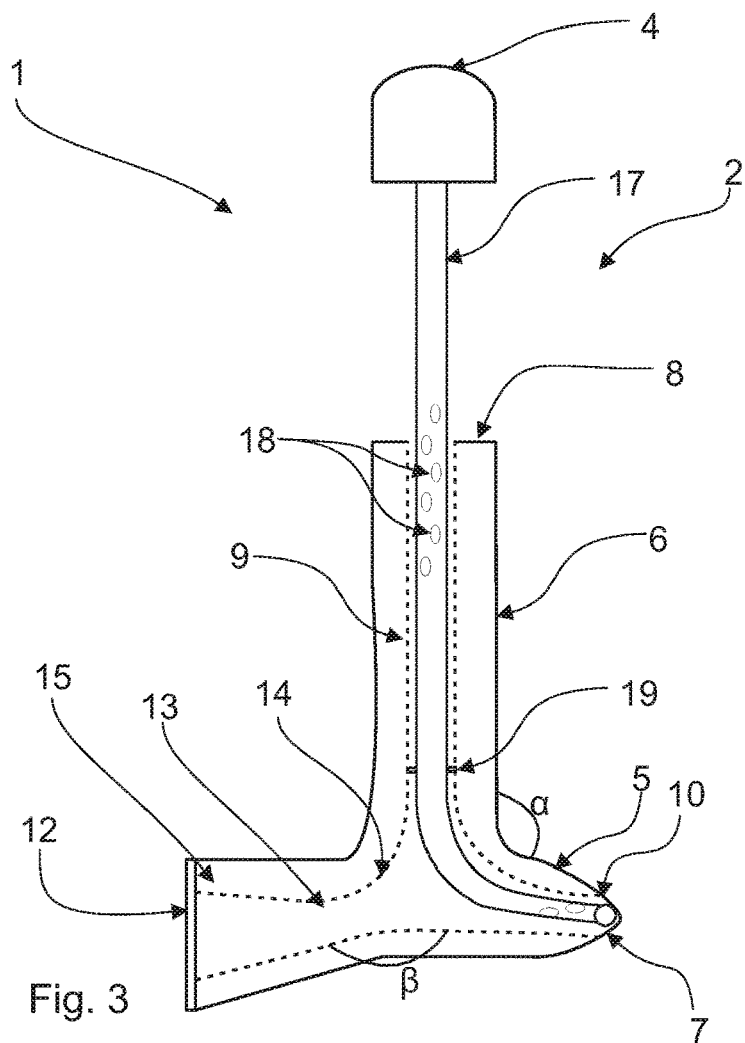
Figure 4:
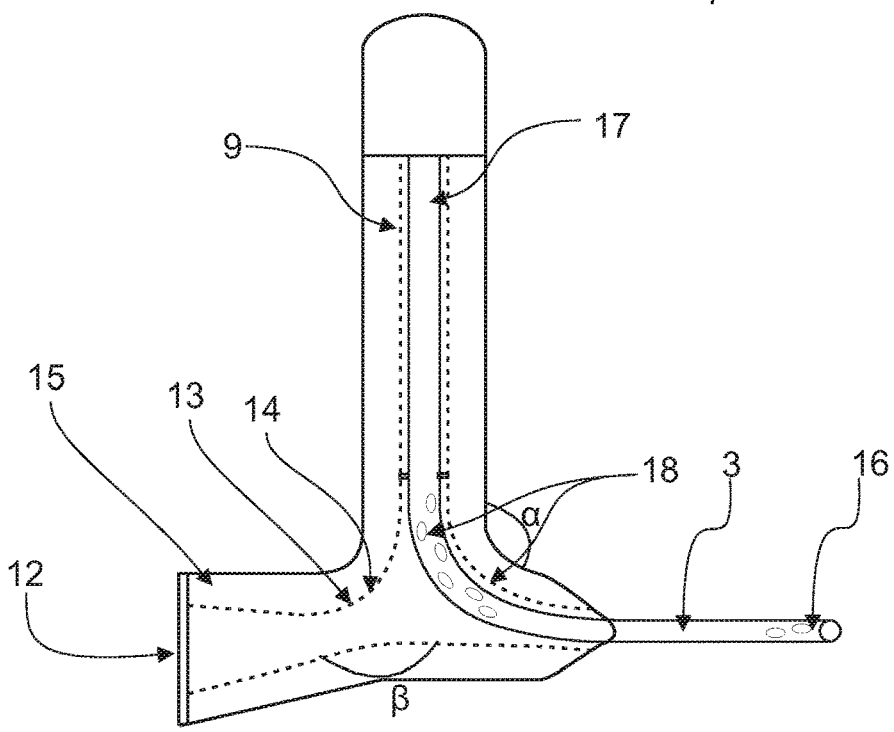

FIGS. 1-4 illustrates an intermittent urinary catheter assembly 1 having a urinary catheterization aid 2 and a catheter 3 provided with a catheter handle 4 at its distal end. The urinary catheterization aid 2 has a handle 5 and an insertion guide 6, the handle 5 provided at a first angle α with respect to the insertion guide 6. The insertion guide has a proximal end 7, and the handle has a distal end 8. A guiding channel 9 extends through the handle 5 and insertion guide 6 from the distal end 8, through the handle to the proximal end 7 where the guiding channel 9 terminates in a proximal opening 10 (the guiding channel is best seen in FIGS. 3-4).

The urinary catheterization aid has an outlet 11. In the embodiment in FIG. 1, the outlet 11 is in the form of a drainage opening 12 in the handle.

In the embodiment illustrated in FIGS. 2-4, the outlet 11 has an outlet channel 13 with a proximal end 14 communicating with the guiding channel 9 of the handle. The outlet channel is at a second angle β with respect to the guiding channel (FIG. 3). The outlet channel 13 terminates in a drainage opening 12 in a distal end 15 of the outlet channel.

The catheter has a proximal insertion end 16 and a distal end 17; the catheter handle 4 being positioned at the distal end 17. In a middle part of the catheter between the proximal end 16 and the distal end 17, drainage holes 18 are provided in the catheter (seen in FIGS. 3 and 4). The catheter may be a telescopic catheter so that the user initially pulls the distal end of the catheter upwards to extend the catheter to a longer configuration (schematically illustrated in FIG. 2) and then subsequently inserts the catheter in a proximal direction by pushing the catheter downwards (see FIG. 2).

The guiding channel 9 is provided with sealing means 19, e.g. in form of a gasket or sealing ring (see FIG. 3).

FIGS. 5-7 illustrate another intermittent urinary catheter assembly 30. The assembly has a urinary catheterisation aid 32 and a catheter 33 having a distal end 34 and a proximal insertion end 35. The urinary catheterisation aid has a handle 36 with a proximal end 37 and a distal end 38. The handle has a guiding channel 39 extending through the handle from the distal end 38 to the proximal end 37. In the figures, the handle 36 is open in the distal end 38. The distal end may also be closed and an outlet 40 provided in a side of the handle—as indicated in FIG. 6.

Alternatively, the handle 36 could be provided with a closure element in cooperation with a distal end 34 of the catheter, so that the distal end 38 of the handle will be closed as long as the catheter is in contact with it.

The urinary catheterization aid illustrated in FIGS. 5 to 7 has means for transferring movement from a second direction to a first direction. These means are in FIG. 5 in the form of a string element 41 attached to a distal end 34 of the catheter. The string element 41 is threaded through a side opening 42 close to the proximal end 37 of the handle. The string element 41 is in the illustrated embodiment provided with a pull-ring 43, allowing for entering a finger through the pull-ring 43.

Figure 8:
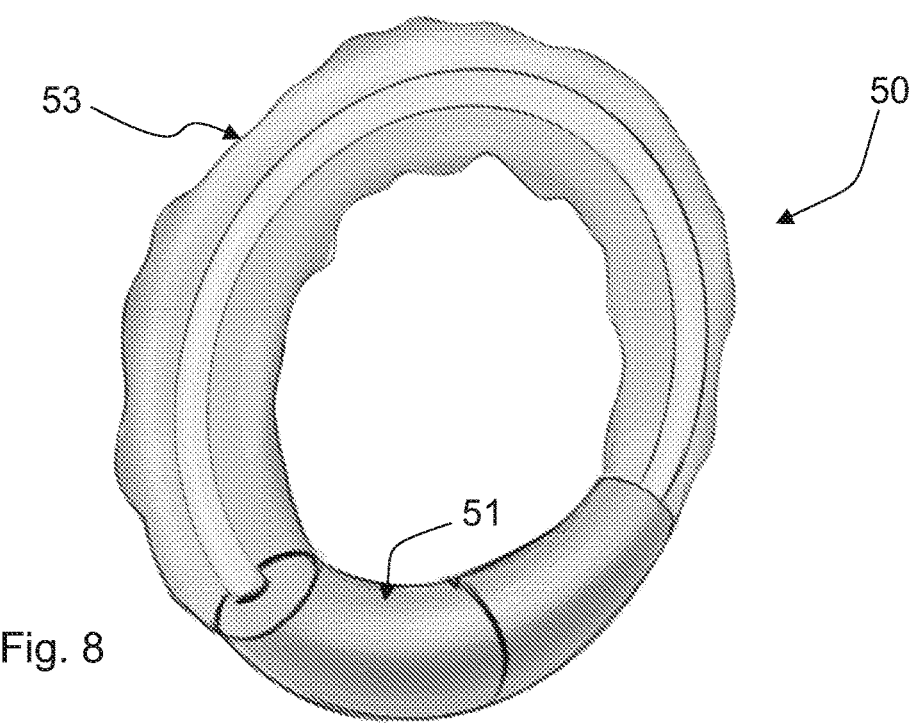
FIGS. 8-9 illustrate another embodiment of an intermittent urinary catheter assembly.
Figure 9:
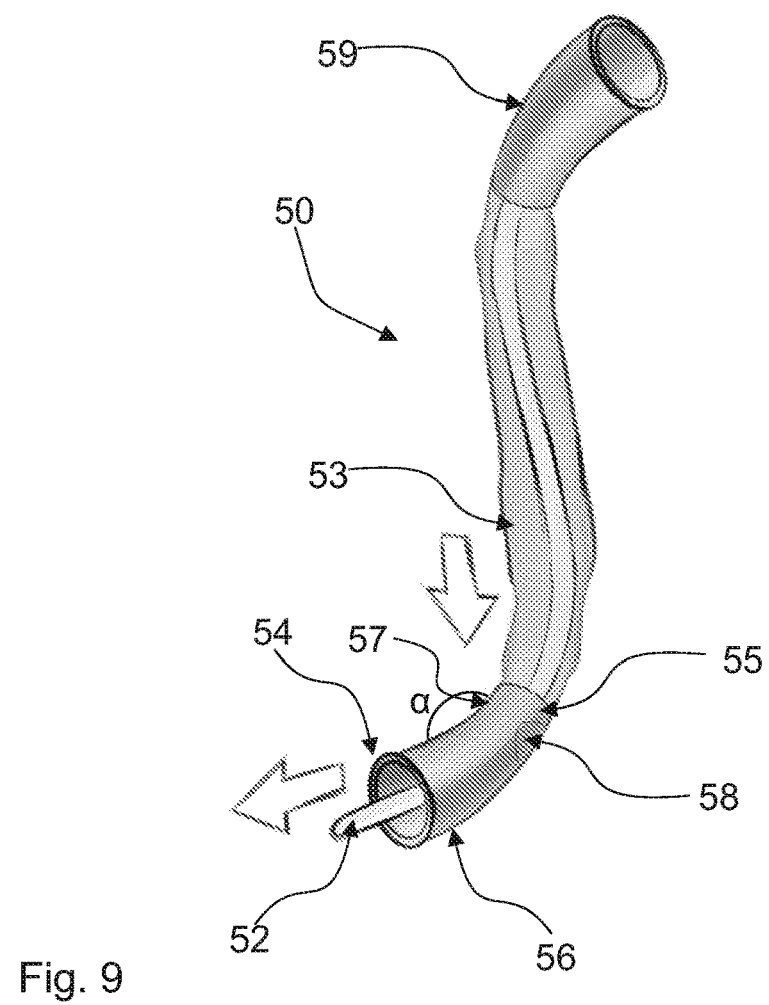

FIGS. 8 and 9 illustrate an intermittent urinary catheter assembly 50. The assembly has a handle and insertion guide provided as one continuously curved element 51 and a catheter 52, the catheter 52 is enclosed in a sleeve 53 in a closed, storage configuration. The handle and insertion guide 51 has a curved configuration such the handle 57 is at a first direction and the insertion guide 56 is at a second direction. Thereby, a proximal end 54 of the insertion guide is angled with a first angle α with respect to a distal end 55 of the handle. This means that a catheter passing through the handle and insertion guide 51 will enter the distal end 55 of the handle at a first direction and exit the proximal end 54 of the insertion guide at a second direction, the latter direction corresponding to the direction of insertion.

The catheter assembly 50 may have an outlet in the form of a drainage opening 58 (in FIG. 9) in the handle so that urine can be drained through this drainage opening. The drainage opening may be in direct communication with the guiding channel (not shown) through the handle and insertion guide. The catheter assembly 50 has a connector 59 in a distal end, and the sleeve 53 may be attached to this connector. In the illustrated embodiment, the handle 51 and the connector 59 is provided with interlocking means (not shown).

The invention claimed is:

1. A urinary catheterization aid comprising: a handle integrated with an insertion guide, the handle having a distal end, a handle section extending from the distal end of the handle to the insertion guide, and the insertion guide extending from the handle section to a proximal end of the insertion guide; a guiding channel formed to extend through the urinary catheterization aid from the distal end of the handle through the proximal end of the insertion guide, where the guiding channel is adapted to guide an intermittent urinary catheter through the guiding channel and out of the proximal end of the insertion guide; a bend section formed between the handle section of the handle and the insertion guide, with the bend section curved at a first angle in a range from 45 degrees to 135 degrees; an outlet channel extending from the guiding channel to a drainage opening formed at an outer surface of the urinary catheterization aid; and the intermittent urinary catheter inserted into the guiding channel, with the intermittent urinary catheter provided with at least one drain hole at a middle portion of the intermittent urinary catheter to allow urine to exit the intermittent urinary catheter through the at least one drain hole and to exit the urinary catheterization aid through the drainage opening.

2. The urinary catheterization aid according to claim 1, wherein the bend section formed between the handle section of the handle and the insertion guide is approximately 90 degrees.

3. The urinary catheterization aid according to claim 1, wherein the outlet channel extends at a second angle from the guiding channel, the second angle between the outlet channel and the guiding channel in a range from 90 degrees to 180 degrees.

4. The urinary catheterization aid according to claim 1, wherein the outlet channel extends at an angle from the guiding channel of approximately 135 degrees.

5. The urinary catheterization aid according to claim 1, further comprising a seal provided in the distal end of the handle, wherein the seal is adapted to prevent urine from exiting the distal end of the handle.

6. The urinary catheterization aid according to claim 1, wherein the bend section is continuously curved along a length of the handle section and the insertion guide.

7. The urinary catheterization aid according to claim 1, wherein the drainage opening is formed in the bend section and the outlet channel communicating between the guiding channel and the drainage opening.

8. The urinary catheterization aid according to claim 1, wherein the intermittent urinary catheter is inserted into the guiding channel, with intermittent urinary catheter provided with an insertion end that is movable into and out of the proximal end of the insertion guide and a distal end, with a catheter handle attached to the distal end of the intermittent urinary catheter.

9. The urinary catheterization aid according to claim 1, wherein the intermittent urinary catheter is inserted into the guiding channel; wherein the intermittent urinary catheter comprises a distal end opposite of an insertion end that is movable into and out of the proximal end of the insertion guide; wherein the intermittent urinary catheter includes a middle portion located between the distal end and the insertion end, with the drain hole formed in the middle portion and a urine entrance hole located between the drain hole and the insertion end.

10. The urinary catheterization aid according to claim 1, wherein the first angle is a permanently formed angle in the range from 45 degrees to 135 degrees.

11. The urinary catheterization aid according to claim 1, wherein the first angle is a permanently formed angle in the range from 45 degrees to 135 degrees, and the bend section is adapted to allow:
   a user to insert the urinary in a first direction into the distal end of the handle, deflection of the urinary
   catheter along the permanently formed angle to a second direction, and
   an exit of the urinary catheter out of the proximal end of the insertion guide in the second direction and into a urethra of the user.

* * * * *